United States Patent [19]

De Vincentiis

[11] 4,440,786
[45] Apr. 3, 1984

[54] COMPOUNDS WITH ANTIFLAMMATORY AND ANALGESIC ACTIVITY, PROCESS FOR THE PREPARATION THEREOF AND PHARMACEUTICAL COMPOSITIONS THEREFROM

[75] Inventor: Leonardo De Vincentiis, Rome, Italy

[73] Assignee: Ausonia Farmaceutici s.r.l., Pomezia, Italy

[21] Appl. No.: 380,124

[22] Filed: May 20, 1982

[30] Foreign Application Priority Data

Nov. 24, 1981 [IT]  Italy ................................ 25245 A/81

[51] Int. Cl.³ ...................... C07C 59/52; A01N 37/12
[52] U.S. Cl. .................................... 424/319; 424/316; 562/569; 260/501.11; 260/501.14; 260/501.17
[58] Field of Search ................ 424/319, 316; 562/569; 260/501.11, 501.14, 501.17

[56] References Cited

U.S. PATENT DOCUMENTS

| 3,755,603 | 8/1973 | Harrison et al. | 562/469 |
| 3,948,973 | 4/1976 | Phillips | 562/469 |
| 4,021,479 | 5/1977 | Seeger et al. | 562/469 |
| 4,151,302 | 4/1979 | Gante et al. | 562/469 |
| 4,188,491 | 2/1980 | Nicholson et al. | 562/469 |
| 4,189,499 | 2/1980 | Tosi et al. | 260/501.11 |
| 4,225,730 | 9/1980 | Jones et al. | 562/469 |
| 4,278,678 | 7/1981 | Hamayaki | 562/469 |

Primary Examiner—James H. Reamer
Attorney, Agent, or Firm—Bucknam and Archer

[57] ABSTRACT

The compound (2',4'-difluoro-4-biphenyl)oxyacetic acid and its pharmaceutically acceptable salts with a metal or an organic base are described. They exhibit high antiinflammatory and analgesic activity and do not cause gastric lesions.

10 Claims, No Drawings

COMPOUNDS WITH ANTIINFLAMMATORY AND ANALGESIC ACTIVITY, PROCESS FOR THE PREPARATION THEREOF AND PHARMACEUTICAL COMPOSITIO NS THEREFROM

DESCRIPTION OF THE INVENTION

The present invention relates to substituted oxyacetic acids and more specifically to novel compounds exhibiting high antiinflammatory activity, high analgesic activity and free from gastric lesion effects. The novel compounds according to the present invention are represented by the compound (2',4'-difluoro-4-biphenyl)oxyacetic acid of formula I:

$$\text{F-C}_6\text{H}_3(\text{F})\text{-C}_6\text{H}_4\text{-O-CH}_2\text{-COOH} \quad (I)$$

and its pharmaceutically acceptable salts with metallic ions, such as sodium, potassium, magnesium, and calcium or with pharmaceutically acceptable organic bases, such as lysine, arginine, diethanolamine. An object of the present invention is to prepare novel compounds exhibiting high antiinflammatory activity and analgesic activity and completely free of gastric lesion effects.

Another object of the present invention is to provide a process for the preparation of the acid of formula I and its salts.

Still another object of the present invention is to provide pharmaceutical compositions and a method of administration of the novel compounds according to the present invention.

The process of preparation of the compound of formula I consists of reacting the sodium salt of 4-(2',4'-difluorophenyl)phenol II with ethylbromoacetate III, obtaining the ester of formula IV and hydrolyzing the ester in accordance with the reaction scheme hereinbelow:

$$\text{F-C}_6\text{H}_3(\text{F})\text{-C}_6\text{H}_4\text{-ONa} + \text{BrCH}_2\text{-COOC}_2\text{H}_5 \longrightarrow$$
$$(II) \qquad\qquad (III)$$

$$\text{F-C}_6\text{H}_3(\text{F})\text{-C}_6\text{H}_4\text{-O-CH}_2\text{-COOC}_2\text{H}_5 \longrightarrow (I)$$
$$(IV)$$

The reaction between compound II and compound III may be carried out in a lower alcohol, preferably ethanol, the compound of formula II being advantageously prepared in situ. The ester of formula IV may be hydrolyzed directly in the crude state with an aqueous solution of an alkali hydroxide. From the solution of the salt of the compound of formula I, the acid of formula I is obtained by acidification with an inorganic acid.

EXAMPLE 1

Method of Preparation

In a flask of 100 cc capacity, sodium in the amount of 0.22 grams is reacted with 30 cc of absolute ethanol. After the sodium has completely gone in solution, there are added 2 grams of 4-(2',4'-difluorophenyl)phenol and then 1.1 cc of ethylbromoacetate. The mixture is allowed to reflux for four hours and then the solvent is evaporated on the vacuum. The residue is treated with 30 cc of 10% sodium hydroxide and allowed to reflux for three hours. After cooling, the solution is acidified with dilute hydrochloric acid. The precipitate is filtered with suction and recrystallized from a mixture of ethyl ether-n-hexane. Yield: 2 grams of the acid of formula I (83%).

The acid melts at 198°–200° C. It is soluble in hot lower alcohols, insoluble in chlorinated hydrocarbons and essentially insoluble in water.

Elementary Analysis: Calcd for $C_{14}H_{10}F_2O_3$ (mol. wt.=264.18); Calcd. %: C=63.65; H=3.81; Found %: C=63.44; H=3.85.

Spectrum IR (nujol mull): 1600 cm$^{-1}$, 1705 cm$^{-1}$, 1730 cm$^{-1}$;

Spectrum H$^1$ NMR (determined in DMSO hexadeuterated, internal reference TMS): 4.7 δ(s, 2H, O—CH$_2$—); 6.8–7.7 δ(m, 7H aromatic, 1H mobile).

The acid of formula I will be referred hereinbelow with the symbol MR 713. The acid is used to prepare the salts in a conventional manner. The examples which follow illustrate the preparation and the properties of some salts of the acid of formula I, but are not intended to be limitative of the invention.

EXAMPLE 2

To a warm solution of 50 grams (0.189 moles) of (2',4'-difluoro-4-biphenyl)oxyacetic acid (I) in 500 cc of ethanol, there are added 10.2 grams (0.189 moles) of pure sodium methoxide. A crystalline solid is formed even in the hot solution and the precipitation is completed by cooling. After recrystallization from water, there are obtained 47 grams of the sodium salt of the compound of formula I; melting point 274°–279° C. (dec.).

Infrared Spectrum—(nujol mull): 1255 cm$^{-1}$, 1580 cm$^{-1}$, 1610 cm$^{-1}$.

EXAMPLE 3

To a warm solution of 0.1 mole of the sodium salt prepared according to Example 2 in 200 cc of water, there is added an aqueous solution of 0.1 moles of calcium chloride in 50 cc of water. By cooling, a crystalline solid precipitates the analytical data of which agree with the following formula:

$$\left[\text{F-C}_6\text{H}_3(\text{F})\text{-C}_6\text{H}_4\text{-O-CH}_2\text{-COO}^-\right]_2 \text{Ca.H}_2\text{O}$$

The substance melts with decomposition above 286° C.

Infrared Spectrum—(nujol mull): 1260 cm$^{-1}$, 1585 cm$^{-1}$, 1660 cm$^{-1}$.

EXAMPLE 4

The acid of formula I, 25 grams, (0.094 moles), is dissolved by warming in 150 cc of ethyl acetate; 5.55 grams, (0.094 moles) of ethanolamine is added. The salt which precipitate partially, even from the warm solution, is isolated by filtration and washed on the filter paper first with ethyl acetate and then with diethyl ether. A crystalline solid, in the amount of 17 grams, is obtained, melting point 164°-167° C.

Elementary Analysis: Calcd. for $C_{16}H_{17}F_2NO_4$ (Mol. Wt.=325.32); Calcd. %: C=59.07; H=5.27; N=4.30; Found %: C=58.88; H=5.33; N=4.24

Infrared Spectrum (nujol mull): 1250 cm$^{-1}$ (asym. stretch C—O), 1580 cm$^{-1}$ (stretch C=C), 1610 cm$^{-1}$ (stretch C=O), 2700-2550 cm$^{-1}$ (stretch N$^+$—H), 3400-3200 cm$^{-1}$ (stretch O—H).

H$^1$ NMR Spectrum (determinated in hexadeuterated DMSO, internal reference TMS): 2.8 δ(t, 2H, $\underline{CH_2}$—OH); 3.5 δ(t, 2H, $\underline{CH_2}$—OH); 4.3 δ(s, 2H, O—$\underline{CH_2}$—CO); 6.4-7.5 δ(m, 11H, aromatic 7H and mobile 4H).

EXAMPLE 5

In analogy with Example 4, but using L-lysine, instead of ethanolamine as the starting material, there is obtained the corresponding salt of L-lysine, melting point 214°-218° C., $[\alpha]_D^{20} = +6.5°$ (c=4.8 methanol).

Elementary Analysis: Calcd. for $C_{20}H_{24}F_2N_2O_5$ (Mol. Wt.=410.41); Calcd. %: C=58.53; H=5.89; N=6.82; Found %: C=58.61; H=5.78; N=6.84.

Antiinflammatory Activity

The experiments have been carried out with rats and carrageenan has been used as the agent causing edema. The product under examination is administered by the oral route in the dose of 25 mg/kg. The substances which are used for comparison purposes have been acetyl salicylic acid (ASA), ibuprofen, paracetamol (p-acetylaminophenol) and diflunisal. The determination of the volume of the paws due to inflammation has been carried out every hour during the five hours subsequent to the treatment.

The results obtained are shown in Table I. On the basis of the data in Table I, it is possible to note that the antiinflammatory activity of MR 713 is essentially the same as diflunisal, is substantially superior to paracetamol even when the latter is used in doses four times larger, lower than that of ibuprofen, (the latter being employed in doses four times larger) and is essentially equivalent to the activity of acetylsalicylic acid, the latter, however, being employed in a dose ten times larger.

Analgesic Activity

The analgesic activity has been tested in mice using the contorsion test caused by phenylquinone. Even in this case, MR 713 has been administered by the oral route in the dose of 25 mg/kg and the same substances used in the edema test have been used for comparison purposes. Phenylquinone has been administered thirty minutes after the substance under test and the results obtained are reported in Table II.

Gastric Tolerability

MR 713 has been administered by the oral route in the dose of 25 mg/kg to rats kept fasting for a period of eighteen hours. After a six hours treatment, the animals have been sacrificed, then the stomach has been extracted for the examination of the gastric mucosa for the purpose of determining possible lesions. For the purpose of comparison, there are used under the same experimental conditions, acetylsalicylic acid, ibuprofen, paracetamol, and diflunisal. The optimum tolerability of MR 713 on the gastric level has been demonstrated by the results obtained and reported in Table III, which show that MR 713 causes even less gastric lesions as compared with drugs which are well-known to be tolerated at the gastric level, such as paracetamol and diflunisal. The same experiment, on the other hand, shows quite clearly that ibuprofen and acetylsalicylic acid cause gastric lesions.

Acute Toxicity

MR 713 presents a very low acute toxicity: its $DL_{50}$ in mice by the oral route is 790 mg/kg of body weight.

TABLE I

ANTIINFLAMMATORY ACTIVITY
Subplantar Edema Caused by Carrageenan in Rats

| Substance | Dose mg/kg/ps | Volume of Paw in No. of Hours after the Treatment | | | | | | AREA Absolute Value | % Inhibition vs. Control |
|---|---|---|---|---|---|---|---|---|---|
| | | 0 | 1 | 2 | 3 | 4 | 5 | | |
| Controls | — | 21.3 | 28.1 | 34.9 | 38.2 | 37.3 | 32.6 | 273.2 | — |
| Acetyl-Salicyclic Acid | 250 | 20.0 | 23.6 | 28.0 | 29.5 | 30.5 | 31.4 | 182.4 | 33.0 |
| Ibuprofen | 100 | 20.3 | 25.2 | 26.5 | 28.7 | 29.6 | 29.9 | 163.7 | 40.0 |
| Paracetamol | 100 | 20.4 | 25.2 | 31.9 | 34.9 | 33.9 | 32.7 | 245.7 | 10.0 |
| Diflunisal | 25 | 21.2 | 25.6 | 29.7 | 31.0 | 33.4 | 33.1 | 190.7 | 30.0 |
| MR 713 | 25 | 21.3 | 24.3 | 29.3 | 31.7 | 33.9 | 33.0 | 186.4 | 31.0 |

TABLE II

ANALGESIC ACTIVITY
Contorsions Caused by Phenylquinone in Mice

| Treatment | Dose mg/kg/os | Average No. of Contorsions | % Inhibition vs. Controls | No. of Animals with Contorsions |
|---|---|---|---|---|
| Control | | 23.5 ± 6.1 | | 10/10 |
| Acetyl | 250 | 0 | 100 | 0/10 |

TABLE II-continued

ANALGESIC ACTIVITY
Contorsions Caused by Phenylquinone in Mice

| Treatment | Dose mg/kg/os | Average No. of Contorsions | % Inhibition vs. Controls | No. of Animals with Contorsions |
|---|---|---|---|---|
| Salycilic Acid | | | | |
| Ibuprofen | 100 | 0.2 ± 0.1 | 99.1 | 2/10 |
| Paracetamol | 100 | 8.6 ± 3.3 | 63.4 | 5/10 |
| Diflunisal | 25 | 0.2 ± 0.2 | 99.1 | 1/9 |
| MR 713 | 25 | 10.8 ± 2.8 | 54.0 | 9/10 |

TABLE III

GASTRIC LESION ACTIVITY

| Treatment | Dose mg/kg/os | Average Size of Ulcer in mm |
|---|---|---|
| Controls | — | 0 |
| Acetyl Salicylic Acid | 250 | 3.7 ± 0.8 |
| Ibuprofen | 100 | 2.3 ± 0.7 |
| Paracetamol | 100 | 0.6 ± 0.4 |
| Diflunisal | 25 | 0.7 ± 0.4 |
| MR 713 | 25 | 0.3 ± 0.1 |

The pharmacodynamic tests carried out in rats and administering MR 713 by the oral route in the doses of 25, 50, and 100 mg/kg, show a half-life time of plasmatic levels, which is possible to calculate in the dose of 25 mg/kg, of about eleven hours. This is a high value at equal dose with respect to common antiinflammatory agents of the nonsteroidal type and particularly substantially superior to the action of diflunisal. The pharmacodynamic tests permit to administer one or at the most two daily doses of MR 713.

The present invention also covers all the industrial applications and use of MR 713 and its salts as antiinflammatory and analgesic agents. A substantial aspect of the invention resides in pharmaceutical formulations which contain predetermined amounts of MR 713 or its salts. The compositions according to the present invention may be administered by the oral or parenteral route, for instance in the form of compresses, capsules, powders, which may be dispersed in water and packaged in small envelopes, phthials suitable for injection. By way of example, the following formulations may be used:

(a) compresses containing 250 mg of (2',4'-difluoro-4-biphenyl)oxyacetic acid with excipients and dispersing agents conventionally used in the pharmaceutical industry;

(b) compresses containing 375 mg of the acid of formula I containing the additional excipients and dispersing agents as above;

(c) phthials containing 400 mg of the lysine salts of (2',4'-difluoro-4-biphenyl)oxyacetic acid which has been lyophilized, together with a phthial of about 3 cc of solvent for intramuscular injetion.

I claim:

1. The compound (2',4'-difluoro-4-biphenyl)-oxyacetic acid of formula I

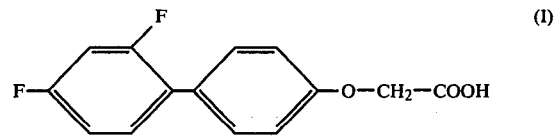

or a pharmaceutically acceptable salt thereof with sodium, potassium, magnesium or calcium or an organic base which is lysine, arginine or ethanolamine.

2. The compound according to claim 1, which is the sodium salt of said acid of formula I.

3. The compound according to claim 1, which is the calcium salt of said acid of formula I.

4. The compound according to claim 1, which is the lysine salt of said acid of formula I.

5. The compound according to claim 1, which is the arginine salt of said acid of formula I.

6. The compound according to claim 1, which is the ethanolamine salt of said acid of formula I.

7. A pharmaceutically composition having antiinflammatory and analgesic activity, which comprises as the active ingredient an effective amount of a compound according to claim 1 and inert excipients.

8. A formulation according to claim 7, which is a composition suitable for oral administration.

9. A pharmaceutical composition according to claim 7 suitable for administration by the parenteral route.

10. The method of treating a living subject affected by pain and/or inflammation, which consists of administering to said living subject an effective amount of (2',4'-difluoro-4-biphenyl)oxyacetic acid or a pharmaceutically acceptable salt thereof.

* * * * *